United States Patent
Shomoto et al.

(10) Patent No.: US 12,090,081 B2
(45) Date of Patent: Sep. 17, 2024

(54) SHOULDER BRACE AND REHABILITATION METHOD USING SHOULDER BRACE

(71) Applicant: FUYUKI ACADEMY, Nara (JP)

(72) Inventors: Koji Shomoto, Osaka (JP); Masanori Fuyuki, Nara (JP)

(73) Assignee: FUYUKI ACADEMY, Nara (JP)

( * ) Notice: Subject to any disclaimer, the term of this patent is extended or adjusted under 35 U.S.C. 154(b) by 430 days.

(21) Appl. No.: 17/604,558

(22) PCT Filed: Mar. 17, 2020

(86) PCT No.: PCT/JP2020/011860
§ 371 (c)(1),
(2) Date: Oct. 18, 2021

(87) PCT Pub. No.: WO2020/217786
PCT Pub. Date: Oct. 29, 2020

(65) Prior Publication Data
US 2022/0192857 A1   Jun. 23, 2022

(30) Foreign Application Priority Data

Apr. 26, 2019   (JP) .................................. 2019-085379

(51) Int. Cl.
*A61F 5/37*   (2006.01)
*A61H 1/02*   (2006.01)

(52) U.S. Cl.
CPC ......... *A61F 5/3738* (2013.01); *A61H 1/0281* (2013.01)

(58) Field of Classification Search
CPC ........... A61F 5/3738; A61F 2201/1238; A61H 1/0274; A61H 1/0277; A61H 1/2081;
(Continued)

(56) References Cited

U.S. PATENT DOCUMENTS 7,245,972 B2 *   7/2007   Davis ................... A61N 1/3787
                                                                    607/46
2003/0018388 A1 *   1/2003   Comer .................. F15B 15/103
                                                                    623/57
(Continued)

FOREIGN PATENT DOCUMENTS

CN   109044726 A   12/2018
CN   109350922 A   2/2019
(Continued)

OTHER PUBLICATIONS

International Search Report dated May 26, 2020 filed in PCT/JP2020/011860.
(Continued)

*Primary Examiner* — Camtu T Nguyen
(74) *Attorney, Agent, or Firm* — Pearne & Gordon LLP

(57) ABSTRACT

A shoulder brace includes a shoulder cuff that can be worn to cover the shoulder of a user, an upper arm cuff that can be worn to cover the elbow joint of the user, a belt that can secure the shoulder cuff to the shoulder of the user, and an actuator that is the McKibben artificial muscle which can optionally expand and contract in entire length. The actuator contains a main actuator to link the vicinity of the acromion on the shoulder cuff and a side face of the upper arm cuff across the shoulder joint, an anterior auxiliary actuator to link a front face of the shoulder cuff and a front face of the upper arm cuff across the shoulder joint, and a posterior auxiliary actuator to link a back face of the shoulder cuff and a back face of the upper arm cuff across the shoulder joint.

2 Claims, 5 Drawing Sheets

(58) Field of Classification Search
CPC .......... A61H 1/0229; A61H 2201/1207; A61H 2201/1635; A61H 2201/1614; A61H 2201/1616; A61H 39/002; A61H 2205/065; A61H 2205/06
See application file for complete search history.

(56) References Cited

U.S. PATENT DOCUMENTS

| | | |
|---|---|---|
| 2007/0004570 A1 | 1/2007 | Afanasenko et al. |
| 2009/0149789 A1 | 6/2009 | Huang et al. |
| 2009/0276058 A1* | 11/2009 | Ueda .................... A61H 1/0274 600/595 |
| 2010/0210985 A1 | 8/2010 | Kuorak et al. |
| 2017/0157396 A1 | 6/2017 | Dixon et al. |
| 2017/0296418 A1 | 10/2017 | Lee |

FOREIGN PATENT DOCUMENTS

| | | |
|---|---|---|
| JP | S60-129044 A | 7/1985 |
| JP | H07-501963 A | 3/1995 |
| JP | 2010-534507 A | 11/2010 |
| JP | 2013-013579 A | 1/2013 |
| JP | 2014-124399 A | 7/2014 |
| WO | 2007-043308 A1 | 4/2007 |
| WO | 2018-065459 A1 | 4/2018 |

OTHER PUBLICATIONS

Office Action mailed on Jun. 11, 2021 for the corresponding Japanese Patent Application No. 2019-085379.
Shoulder joint brace for pulling up the upper extremity "Omo Neurexa Plus," retrieved from website of Ottobock Japan K.K. <https://www.co.jp/orthotic/upper/shoulder/omo_neurexa_plus/> on Apr. 15, 2019.

* cited by examiner

<KNOWN TECHNOLOGY>

<PRESENT INVENTION>

SHOULDER BRACE AND REHABILITATION METHOD USING SHOULDER BRACE

TECHNICAL FIELD

The present invention relates to a shoulder brace, and more particularly a shoulder brace used in rehabilitation of a patient to improve shoulder joint inferior subluxation caused by stroke hemiplegia. The present invention also relates to a rehabilitation method using the shoulder brace.

BACKGROUND ART

A patient of stroke hemiplegia often experiences inferior subluxation of the shoulder joint (scapulohumeral joint) when he or she has experienced flaccid paralysis at the onset or for a long period after the onset. It is said that shoulder joint inferior subluxation occurs when factors such as paralysis of muscles surrounding the shoulder join, elongation of coracohumeral ligaments, loss in proprioception of the upper extremity and shoulder girdle, shortening of the pectoralis major muscle and latissimus dorsi muscle, and gravity influence one another. Especially, it is known that when a patient treated in the supine position at the onset of stroke sits up or stands up thereafter, the weight of the arm by gravity is applied to the shoulder joint with flaccid paralysis, which often causes occurrence of shoulder joint inferior subluxation.

In the normal shoulder joint, strains of the deltoid muscle and the supraspinatus muscle mainly act in cooperation so as to push the head of the humerus against the glenoid cavity of the scapula. Also, the infraspinatus muscle, the teres minor muscle, and the subscapularis muscle, which are collectively called the "rotator cuff (rotator muscles)", also act in a similar manner for stabilization in the back-and-forth direction. On the other hand, in a stroke hemiplegia patient, paralysis of these muscles surrounding the shoulder joint causes the scapula to be pulled outward and downward by the weight of the upper extremity to cause downward rotation. Accordingly, the head of the humerus often drops downward to develop subluxation as illustrated in FIG. 1.

Shoulder joint inferior subluxation also occurs due to an accident in which the shoulder is hard hit, such as accidental falling or collision in sports. A common treatment thereof is, after reducing subluxation, immobilizing the shoulder joint at an appropriate position with a so-called arm sling and waiting for recovery of the relaxed or ruptured ligament or the like, and thereafter performing various rehabilitation works. On the contrary, in a stroke hemiplegia patient with, for example, relaxation of muscles surrounding the shoulder joint, rehabilitation is generally performed for an extended period, and often performed with an arm sling worn.

An arm sling is largely classified into an elbow joint flexion type and an elbow joint extension type. The elbow joint flexion type is easy to wear and provides strong supporting power, but immobilizes the humerus at the adduction and internal rotation position. Therefore, when it is continuously worn for a long time, not only the arm muscle such as the biceps muscle may contract, but also rehabilitation with an arm sling worn is restricted. Since it is desirable to retain the shoulder joint with the elbow stretched and allow flexion and extension of the elbow in rehabilitation to improve shoulder joint inferior subluxation caused by stroke hemiplegia, the elbow joint flexion type is rather not appropriate.

On the other hand, the elbow joint extension type generally has a form in which a shoulder cuff (or a shoulder pad) and an upper arm cuff or a forearm cuff are linked with a belt or the like to lift the arm. The elbow joint extension type is excellent in that the shoulder joint can be appropriately immobilized. However, for supporting the weight of the arm by the upper arm cuff, strong constriction is necessary in the cuff portion so as to obtain sufficient lifting power. This may cause a circulatory deficit. On the contrary, for supporting the weight of the arm by the forearm cuff, there were problems as follows: it is inconvenient to adjust a traction force corresponding to the body shape and the arm weight of a patient (that is, a user); mobility of the elbow joint is likely to be restricted; it is difficult to properly wear by oneself; and a corrective force extremely varies depending on a traction direction.

For solving such problems, for example, Patent Document 1 discloses, as a known technology, a shoulder brace which further includes a forearm cuff linked to an upper arm cuff through a tension band so that flexibility in mobility of the elbow joint can be ensured while a traction force can be adjusted. This known technology has been already commercialized and become widespread as a shoulder joint brace for pulling up the upper extremity indicated in Non-Patent Document 1.

Patent Document 1: JP-T-2010-534507

Non-Patent Document 1: Shoulder joint brace for pulling up the upper extremity "Omo Neurexa Plus", website of Ottobock Japan K. K. (https://www.ottobock.co.jp/orthotic/upper/shoulder/omo_neurexa_plus/)

However, the shoulder brace according to such known technology has a structure in which the weight of the arm is supported by a traction force of the tension band linking the upper arm cuff and the forearm cuff. Accordingly, unless the tension band is in intimate contact along the upper arm and the forearm in a strained state when the shoulder brace is worn, the weight of the arm cannot be sufficiently supported. Thus, for a user whose relaxation degree of muscles surrounding the shoulder joint is severe, the effect of retaining the shoulder joint cannot be sufficiently exerted in some cases. Therefore, it is actually not rare that a user performs rehabilitation without noticing that subluxation is not reduced. Conversely, in a state in which the tension band is strained to sufficiently support the weight of the arm, flexion and extension of the elbow joint becomes difficult. This raised a problem in that possible rehabilitation works are restricted.

On the other hand, since shoulder joint subluxation in a stroke hemiplegia patient is often caused by general paralysis of muscles surrounding the shoulder joint including the rotator cuff, not only inferior subluxation by the weight of the arm but also anterior subluxation (so-called "anterior dislocation") and posterior subluxation (so-called "posterior dislocation") as illustrated in FIG. 2 are also likely to occur. However, in the known technology in which the weight of the arm is supported by a strain force itself of the tension band disposed to the front and back of the arm, adjusting the tension band to deflect a strain force in the back-and-forth direction led to a risk that the vertical direction of a traction force for the arm may be dislocated. In addition, the adjustment itself was also inconvenient.

Rehabilitation to improve shoulder joint subluxation generally involves motions such as motion of the arm in the back-and-forth direction, rotation of the arm, flexion and extension of the elbow joint, and drawing a letter and a figure with a writing material in the hand. Therefore, a shoulder brace used in rehabilitation desirably not only is easy to wear by a user oneself, but also enables the above-described various motions in a state in which the shoulder brace is worn, and is refinable in strength and direction of a traction force as necessary.

Although the shoulder brace according to the known technology is supposed to be wearable by a user oneself and easily adjustable in a strain force of the tension band, it is not necessarily easy in a practical sense to be worn by a user oneself. A user has to put the arm through a tubular shoulder cuff, place a belt around the shoulder on a side without paralysis from the back in such a manner as to wear a sweater, immobilize the shoulder joint using a tension band disposed to the front and back of the shoulder after a shoulder cuff has been worn, and then adjust the length of a pull-up strap linking a shoulder cuff and a forearm cuff so as to fit the length of the arm. Furthermore, the wearing of the forearm cuff and the adjustment in the length of the pull-up strap also have to be performed with the arm placed on a table or the like. Moreover, since the adjustment of the tension band and the pull-up strap needs to be performed while twisting the upper body every time, accurate adjustment in consideration of correction of anterior dislocation and posterior dislocation was not easy, and refinement of the traction force and the traction direction as necessary during rehabilitation was inconvenient.

Furthermore, since the shoulder cuff and the forearm cuff according to the known technology have to be always fixed in intimate contact with the shoulder and the arm, the shoulder cuff has a shape to cover the entire surface from the shoulder to the axilla side of the upper part of the upper arm, and the forearm cuff also has a shape to cover the entire surface from the elbow to the front forearm portion. Since the cuffs are formed of a cloth backed with a non-slip silicon material, irritation to the skin of a user was also caused.

SUMMARY OF THE INVENTION

Problems to be Solved by the Invention

For solving such problems of the known technology, the present invention is an elbow joint extension-type arm sling in which a light actuator capable of expanding and contracting in entire length to an optional length in response to external input and output is adopted in place of the tension belt, as a structure to support the weight of the arm and a measure to adjust a traction force. Accordingly, the present invention has as its object to provide a shoulder brace suitable for use in rehabilitation to improve shoulder joint inferior subluxation caused by stroke hemiplegia, which is easy to wear and freely adjustable in the traction force for the arm and the direction of traction as necessary even after worn.

For solving the above-described problems, the shoulder brace of the present invention includes at least a shoulder cuff that can be worn to cover the shoulder of a user, an upper arm cuff that can be worn to cover the elbow joint of the user, a belt that can secure the shoulder cuff to the shoulder of the user, and an actuator made of a McKibben artificial muscle that can optionally expand and contract in total length in response to external input and output. The actuator contains a main actuator to link a side face of the shoulder cuff and a side face of the upper arm cuff across the shoulder joint, an anterior auxiliary actuator to link a front face of the shoulder cuff and a front face of the upper arm cuff across the shoulder joint, and a posterior auxiliary actuator to link a back face of the shoulder cuff and a back face of the upper arm cuff across the shoulder joint. The upper end of the main actuator is fixed at a position on the inner side than the shoulder joint on the upper face of the shoulder cuff Whereas the shoulder brace according to the known technology lifts the arm and immobilizes the shoulder joint at an optimum position by linking the shoulder cuff and the forearm cuff fixed to the forearm with the tension belt to perform traction, the shoulder brace according to the present invention links the shoulder cuff and the upper arm cuff fixed to the upper arm including the elbow joint with the actuator capable of expanding and contracting to perform traction. It is the main actuator, disposed on the side faces of the shoulder cuff and the upper arm cuff (that is, a side of the body side face along the shoulder to the upper arm) across the shoulder joint, to contract for mainly supporting the weight of the arm to perform upward traction. The upper end of the main actuator is fixed at a position above the clavicle closer to the neck than the shoulder joint on the upper face of the shoulder cuff. With only the main actuator, the traction force acts such that the arm moves away from the body side and opens upward.

On the other hand, the auxiliary actuators disposed on the front and back sides of the body across the shoulder joint also play a role of supporting the weight of the arm to perform upward traction. While contracting, a traction force acts in such a direction as to lift the arm while the anterior auxiliary actuator and the posterior auxiliary actuator respectively rotate the arm to the front and the back of the body. This competes with the force of the main actuator to move the arm away from the body side and open it upward. Thus, the arm is pulled upward to retain the shoulder joint at an appropriate position.

As illustrated in FIG. 3, the glenoid cavity of the scapula is generally positioned upward with an angle of about 5° in a normal state, and a ball called the humerus head is supported by a receiving pan called the glenoid cavity. Therefore, for reducing inferior subluxation, it is desirable that a traction force to lift the arm acts as upward as possible. However, a traction force sufficient to lift the arm upward is not obtained by the structure of lifting the arm only with the tension belt on the front and back of the shoulder, like in the shoulder brace according to the known technology. Thus, subluxation was not completely reduced in rehabilitation in some cases. Also, the traction force could not be easily adjusted in the front and back direction.

Also, in reduction and rehabilitation of shoulder joint subluxation, adjustment in the direction of a traction force to lift the arm is important, because there are differences in build, skeleton, and symptom among users. However, in the shoulder brace according to the known technology, the direction of a traction force is fixed, because the tension band to pull up the arm is disposed to the front and back faces of the shoulder as described above. Also, since it is configured that a traction force is inherently not adequately exerted unless the entire inner surface of the shoulder brace is in intimate contact with the body, a traction force could not be applied with an appropriate magnitude and in an appropriate direction, when the option in size is only S, M, and L, and the size does not sufficiently fit the body of a user. However, when the size is personalized, a problem is naturally raised in that the cost is high.

On the other hand, in the shoulder brace according to the present invention, the main actuator is disposed on a side of the body side face along the shoulder to the upper arm, and the main actuator can be expanded to a position across the subluxated shoulder joint by fixing the upper end of the main actuator at a position above the clavicle closer to the neck than the shoulder joint on the upper face of the shoulder cuff.

For an actuator to contract in response to external input, the stroke of contraction can be generally made larger as the entire length is longer. Therefore, a traction force can be increased by expanding the entire length of the main actuator. Also, since traction forces of the anterior and posterior auxiliary actuators also contribute to the effect of lifting the arm, a sufficient traction force can be exerted. Accordingly, even when a separate actuator has a relatively small power, the shoulder joint can be effectively supported.

Also, since the main actuator can contract so as to exert a traction force in a direction close to vertically upward along the axis of the humerus, a state in which the humerus head is, with an adequate angle, in contact with the glenoid cavity positioned upward with an angle of about 5° as described above becomes easily retained.

Furthermore, a traction force can be applied such that the humerus head is in contact with the somewhat upward glenoid cavity with the corresponding angle as illustrated in FIG. 4, by appropriately adjusting traction forces of the main actuator and the anterior and posterior auxiliary actuators. This enables more appropriate immobilization of the shoulder joint and also facilitates adjustment of a traction force in the front and back direction. Accordingly, the direction of a traction force can be optimized corresponding to differences in build, skeleton, and symptom among users, and furthermore, corresponding to the type and purpose of motions in rehabilitation.

Among so-called actuators (drivers), the McKibben artificial muscle is obtained by covering the outer periphery of an elastic body tube made of natural rubber, urethane rubber, or the like with a tubular spiral mesh sleeve woven of synthetic resin fiber, fixing and blocking the both ends by a pair of terminals having an air breathing mechanism. The elastic body tube is expanded by externally applied air pressure such that the entire length contracts. When the angle of mesh of the sleeve changes like an accordion, the diameter increases in response to axial pushing, and conversely, the diameter decreases in response to pulling. In principle, when the internal elastic body tube is to expand in the axial direction and in the diameter direction in response to applied air pressure, the angle of mesh of the sleeve changes following the expansion in the diameter direction, which causes the elastic body tube to have a contraction force in the axial direction.

Compared to an electromagnetic or hydraulic cylinder actuator, the McKibben artificial muscle has the following merits: light and high power density (large power is produced despite a small self weight), excellent environmental resistance (high tolerance to rust and dirt), simple structure and easy maintenance, high flexibility and characteristics similar to human muscles, and low production cost.

A shoulder brace for rehabilitation to be directly worn by the human body and repeatedly used is required to have a light, simple, and flexible structure, characteristics similar to human muscles, easiness in adjustment and maintenance, and endurance to repeated use for a long period. Therefore, it can be said that the McKibben artificial muscle is suitable as the actuator in the present invention.

When the McKibben artificial muscle is used, one terminal thereof is connected to an exchangeable steel gas cylinder through a tube, and a pressure adjusting valve is disposed therebetween. These devices can be made compact and light, which alleviates the burden of a user. Also, once the shoulder brace is worn, a traction force can be refined through individual operation of a necessary actuator, by operating the pressure adjusting valve close at hand, without taking a posture of, for example, twisting the upper body. Therefore, the symptom and recovery degree of a user, the type of motion to be performed in rehabilitation, and the like can also be flexibly accommodated.

Next, the present invention relates to the shoulder brace, in which the upper arm cuff can immobilize the elbow joint from the back side and has a shape to allow flexion and extension of the elbow joint of the user when worn.

As previously described, the shoulder brace according to the present invention does not immobilize the forearm like the shoulder brace according to the known technology, but pulls up the arm while fixing the upper arm above the elbow with the upper arm cuff that can be worn to cover the elbow joint of a user. Therefore, the upper arm cuff does not need to be in intimate contact with the entire circumference of the upper arm, as long as the elbow joint can be immobilized from the back side in the vicinity of the humeral capitulum located on the lower end of the humerus. Therefore, a side corresponding to the introflection side of the elbow joint of the upper arm cuff is opened, so that flexion and extension of the elbow joint of a user is allowed when the shoulder brace is worn. Accordingly, a user can freely perform flexion and extension of the elbow without significant prejudice to a traction force to the arm, and flexibility of rehabilitation can be improved.

Lastly, the present invention relates to a rehabilitation support apparatus of shoulder joint inferior subluxation, obtained by connecting an electrical stimulation apparatus to the shoulder brace, wherein functional electrical stimulation (FES) can be added to shoulder girdle muscles of a user who wears the shoulder brace.

Functional electrical stimulation (FES) is a treatment to improve central motor paralysis caused by stroke and spinal cord injury. When the central nervous system is injured, but the secondary motion neurons is normal, electrical stimulation is directly added to secondary motion neurons by a surface electrode to be stuck on the skin, a percutaneous electrode to be subcutaneously implanted through a wire, a completely implanted electrode to be implanted together with a receiver like a cardiac pacemaker, and the like, such that muscular contraction occurs. This technique is also a potential measure in rehabilitation to improve shoulder joint inferior subluxation caused by stroke hemiplegia.

Recently, hybrid FES in combination with a shoulder brace has been performed. With the shoulder brace according to the known technology, which mainly intends to immobilize the subluxated shoulder joint, not only flexibility in flexion and extension of the elbow joint was restricted, but also adjustment of a traction force corresponding to the type of motion was inconvenient. This posed severe restrictions on application to rehabilitation in combination with FES. However, in combination with the shoulder brace according to the present invention, in which flexibility of flexion and extension of the elbow joint is high, and the magnitude and direction of a traction force can be adjusted at any time even after the shoulder brace has been worn, more effective hybrid FES is enabled.

Effects of the Invention

As described above, the shoulder brace according to the present invention exerts excellent effects as follows.
(1) Self wearing is easy, and setting of a traction force when wearing is also easily.
(2) A traction force to lift the arm larger than in the shoulder brace according to the known technology can be exerted.

(3) The direction of a traction force to lift the arm can be made close to vertically upward.
(4) The magnitude and direction of a traction force can be simply adjusted at any time even after worn.
(5) Not only the arm is pulled upward, and the weight of the arm is supported, but also a traction force can be refined in the horizontal direction and the back-and-forth direction.
(6) Flexion and extension of the elbow joint is facilitated, and flexibility of rehabilitation is high.
(7) When worn, the shoulder brace is not necessarily in intimate contact with the entire circumference of the shoulder and the arm for constriction, and thus air permeability is easily ensured, and the burden of a user is small.
(8) By adopting the McKibben artificial muscle, a powerful traction force can be exerted with a light and simple structure, and the cost is low.

DESCRIPTION OF THE EMBODIMENTS

Hereinafter, embodiments of the present invention will be described based on the drawings. FIG. 5 is a side view of a shoulder brace 1 (for the right shoulder) according to an embodiment of the present invention. When worn, the right side is the front of the wearer, and the left side is the back. FIG. 6 is a front view thereof, and FIG. 7 is a schematic view illustrating a wearing state of the shoulder brace 1. A user wears the shoulder brace 1 with a belt B crossed from the normal left shoulder to the back.

In the shoulder brace 1, a shoulder cuff 10 shaped to be wearable to cover the shoulder of a user is linked to an upper arm cuff 11 that can be worn to cover the elbow joint of the user by four main actuators M1, an anterior auxiliary actuator M2, and a posterior auxiliary actuator M3, which are McKibben artificial muscles. The actuators M1 to M3 are fixed and blocked at both ends by a pair of terminals t. The terminals t on the lower end are connected to tubes p1 to p3 such that air from a steel gas cylinder G can be breathed. Also, a belt B securable around the shoulder of the user is disposed to the upper part of the shoulder cuff 10.

The shoulder cuff 10 is suitably made of hard resin having recoverable elasticity even if it is somewhat deformed when attached to and detached from the shoulder. The shoulder cuff 10 has a shape to cover a site from the shoulder to the upper part of the upper arm of the user and open toward the axilla side of the user. The shoulder cuff 10 is worn in such a manner as to cover the shoulder to the upper arm, instead of putting the upper arm through it, and can be fixed to the upper arm with a strap S which is adjustable in length.

The upper arm cuff 11 is also suitably made of hard resin having recoverable elasticity even if it is somewhat deformed when attached to and detached from the upper arm. The upper arm cuff 11 has a substantially cylindrical shape to cover a site from the lower part of the upper arm to the elbow joint of the user from the back side and open toward the inside of the elbow joint. The upper arm cuff 11 is worn in such a manner as to cover the lower part of the upper arm, instead of putting the forearm through it, and can be fixed to the upper arm with a strap S which is adjustable in length. A portion of the upper arm cuff 11 covering the back side of the elbow joint has a shape capable of fastening the humeral capitulum with the strap S from the back side, while a portion inside the elbow joint has an opened shape. This allows flexion and extension of the elbow joint of the user when the shoulder brace is worn. Also, when the upper arm cuff 11 is fixed in such a manner as to cover the back side of the elbow joint, the lower parts of the biceps muscle and the triceps muscle do not need to be excessively constricted with the strap S, which can alleviate compression on blood circulation and nerves.

It is noted that a liner (inner lining) having cushion properties and non-slip effects is desirably disposed to the inner surface sides of both the shoulder cuff 10 and the upper arm cuff 11 which are brought into contact with the body surface of the user.

The material and shape of the cuffs are not limited to the above-described hard resin, as long as the shoulder cuff 10 and the upper arm cuff 11 respectively immobilize the shoulder and the elbow joint of the user to achieve structural strength that allows transmission of traction forces of the actuators M1 to M3. For example, a hole or a slit for ensuring air permeability may be disposed on the surface, or mesh fabrics may be stretched over a frame structure made of a rigid and soft material.

The upper end side and the lower end side of the four main actuators M1 are respectively mounted to a position slightly on the back side of the acromion on the upper part of the shoulder cuff 10 and to a position on the back side of the elbow joint on the central part of the upper arm cuff 11. The upper end side and the lower end side of the anterior auxiliary actuator M2 are respectively mounted to around a position of the coracoid process of the scapula on the upper chest side of the shoulder cuff 10 and to around a position outside the elbow joint on the central part of the upper arm cuff 11. The upper end side and the lower end side of the posterior auxiliary actuator M3 are respectively mounted to around the upper part of the scapula on the upper back side of the shoulder cuff 10 and to a position inside the elbow joint on the central part of the upper arm cuff 11.

The actuators M1 to M3 are each mounted to the shoulder cuff 10 and the upper arm cuff 11 with a plurality of attachment members f1 and f2. The attachment member f1 is a member for fixing the upper end and the lower end of the actuators M1 to M3 to link the shoulder cuff 10 and the upper arm cuff 11. On the other hand, the attachment member f2 is not for detaining the actuators M1 to M3, but is a member for merely retaining the position of the actuators M1 to M3 without interfering with expansion and contraction of the actuators and the enlargement and shrinkage of the diameters.

One terminal of the tubes p1 to p3 is mounted to the terminal t on the lower end of the actuators M1 to M3, and the other terminal is connected to connectors c1 to c3. The tubes are further connected to the steel gas cylinder G via pressure adjusting valves V1 to V3 illustrated in FIG. 7. The connectors c1 to c3 are disposed for facilitating handling such that the pressure adjusting valves V1 to V3 and the steel gas cylinder G are detachable from the shoulder brace 1.

A user can wear the shoulder brace 1 by putting the belt B over the normal shoulder in a crossed manner, putting the shoulder cuff 10 over the shoulder to the upper part of the upper arm and securing it with the strap S, and then putting the upper arm cuff 11 on the elbow joint from the back and securing it with the strap S. After worn, the shoulder brace 1 can be used by connecting with the steel gas cylinder G and the pressure adjusting valves V1, V2, and V3 individually corresponding to the connectors c1, c2, and c3.

According to the shoulder brace 1, the shoulder cuff 10 and the upper arm cuff 11 do not need to be lifted after the arm has been previously put through them, like the shoulder brace according to the known technology. Therefore, the shoulder brace 1 can be put from the outside and secured with the strap S while retaining the stretched arm, without particularly twisting the upper body when wearing. Thus, self wearing is remarkably easy. Also, if the steel gas cylinder G and the pressure adjusting valves V1 to V3 are unified into one operation unit to be portable, a user can always freely adjust traction forces of all the actuators with a normal hand.

Rehabilitation is performed while operating the pressure adjusting valves V to adjust the traction forces of the actuators and checking a reduced state of shoulder joint subluxation. Especially, when a tendency of anterior dislocation or posterior dislocation is observed in the shoulder joint, rehabilitation is desirably performed while appropriately refining a balance in traction force between the anterior and posterior auxiliary actuators M2 and M3 with the pressure adjusting valves V2 and V3 to prevent the tendency.

A specific structure of the shoulder brace according to the present invention has been described above. However, the present invention is not limited to the above-described embodiments. Improvement or modification thereof is possible within the scope of the technical idea of the present invention, which belongs to the technical scope of the present invention.

INDUSTRIAL APPLICABILITY

The present invention is usable in the treatment of shoulder joint inferior subluxation in general caused by various factors, and is particularly effective in rehabilitation for a patient who experiences shoulder joint inferior subluxation caused by stroke hemiplegia. Also, the effect of the hybrid FES in combination with functional electrical stimulation (FES) can be expected to improve.

Figure 1:
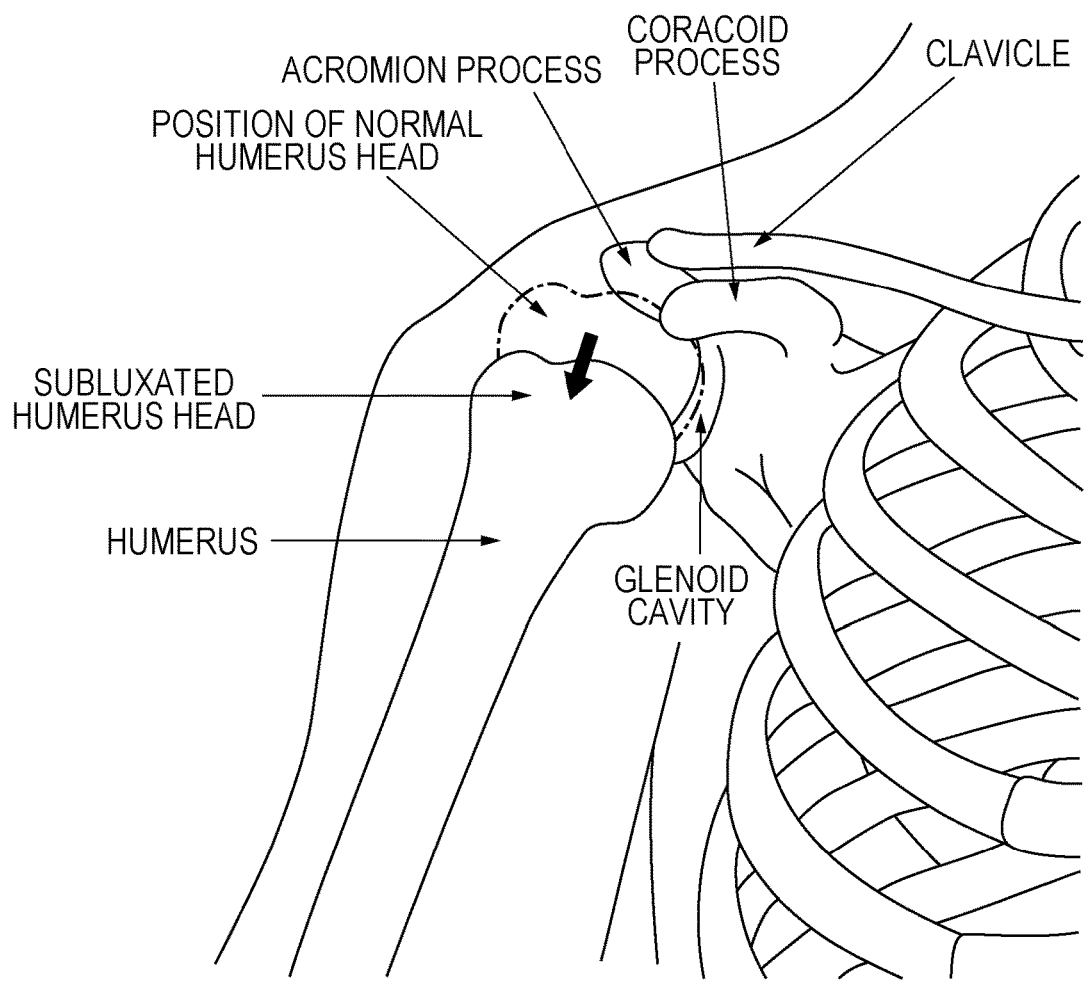
FIG. 1 is a schematic view of shoulder joint subluxation (inferior luxation).
Figure 2:
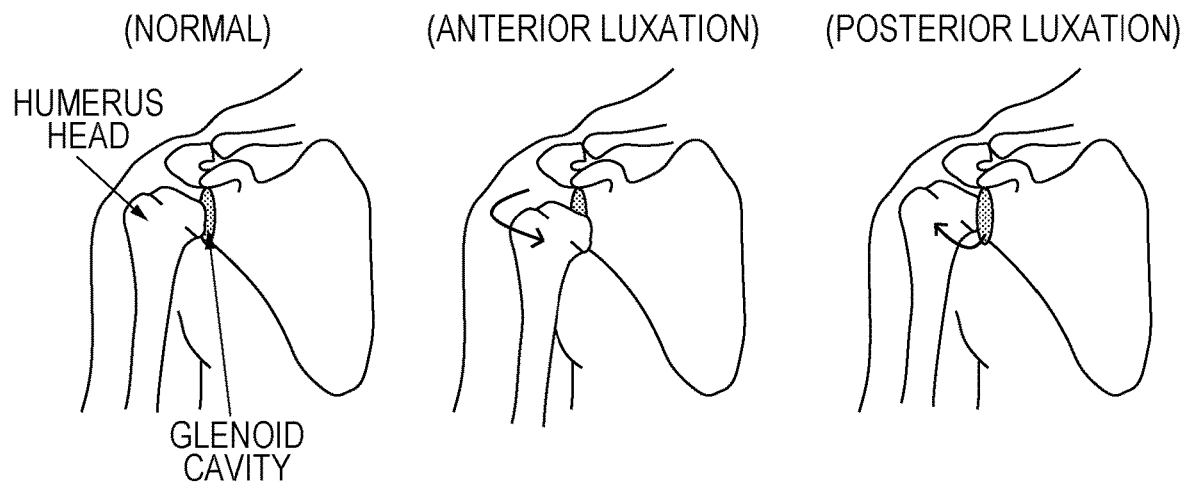
FIG. 2 is a schematic view of shoulder joint subluxation (anterior luxation and posterior luxation).
Figure 3:
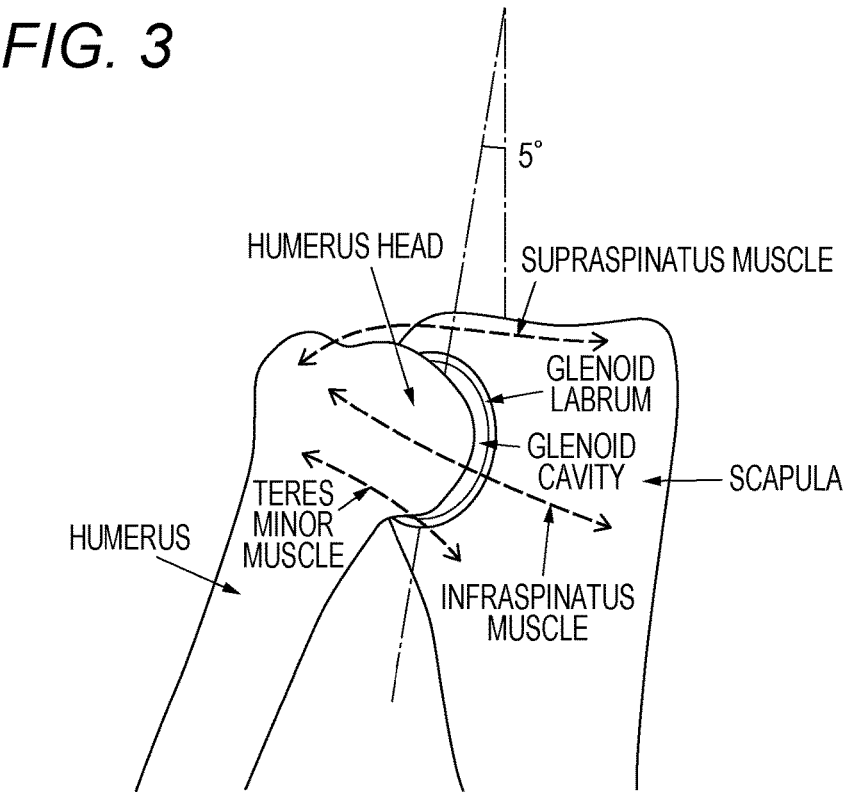
FIG. 3 is a schematic view of a positional relationship between the glenoid cavity and the humerus head.
Figure 4:
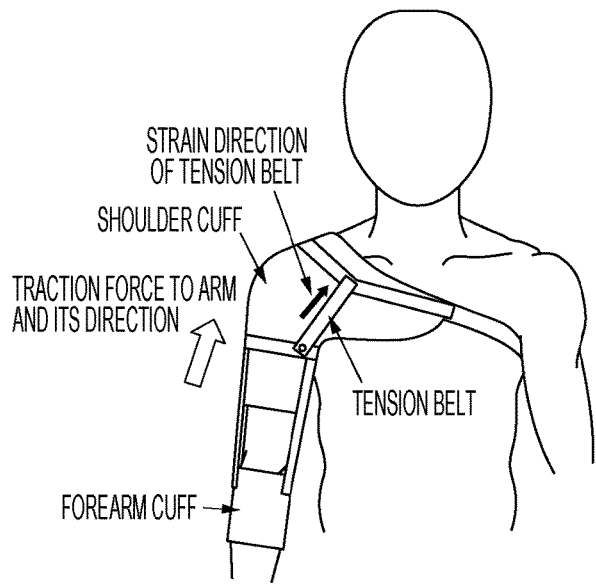
FIG. 4 is a schematic view illustrating a difference in structure between a known technology and the present invention.
Figure 4:
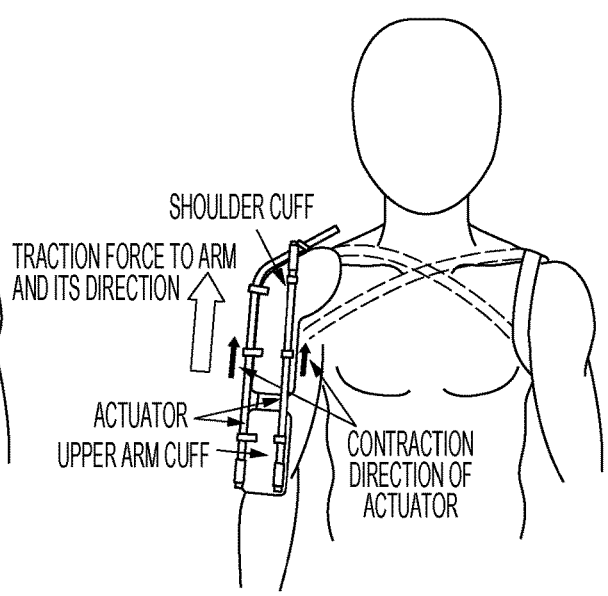
Figure 5:
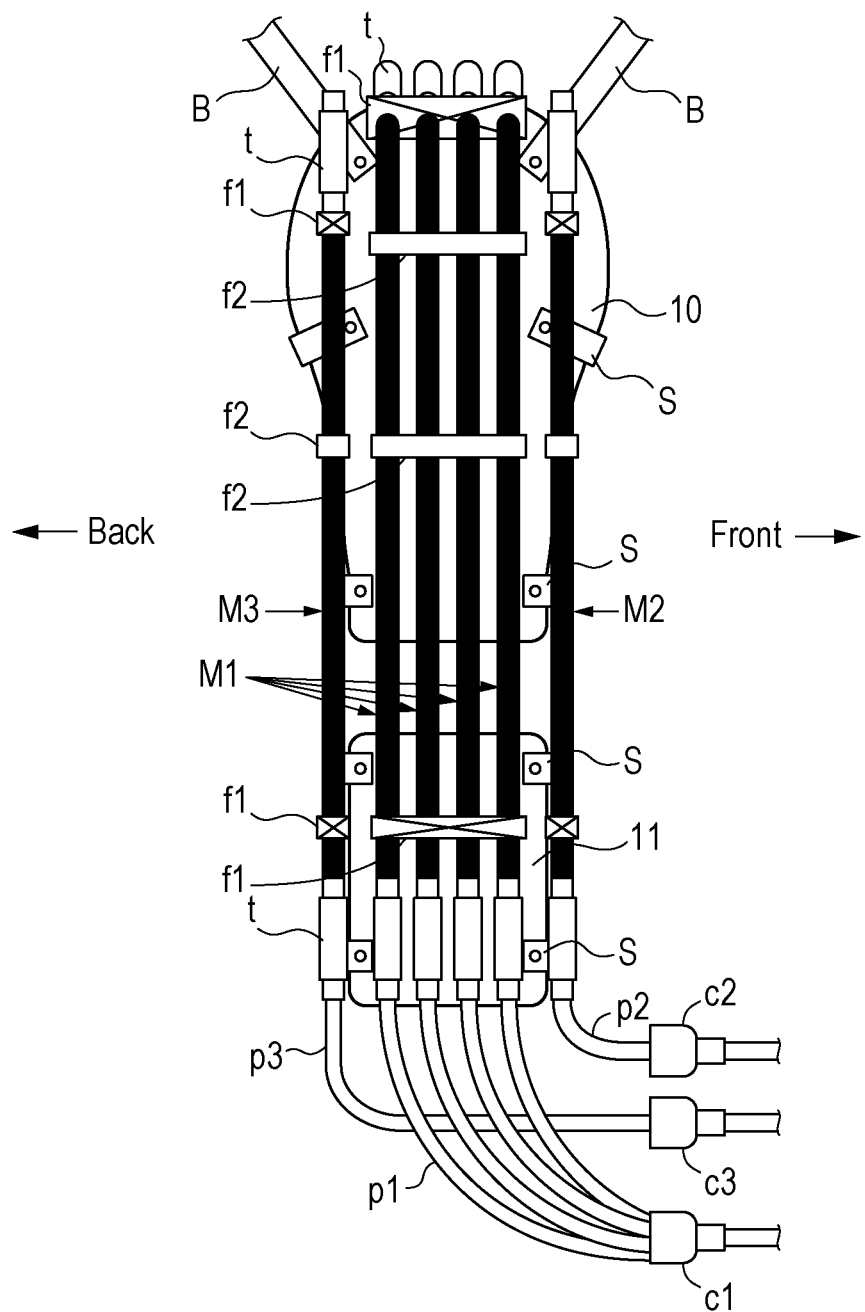
FIG. 5 is a side view of a shoulder brace according to an embodiment.
Figure 6:
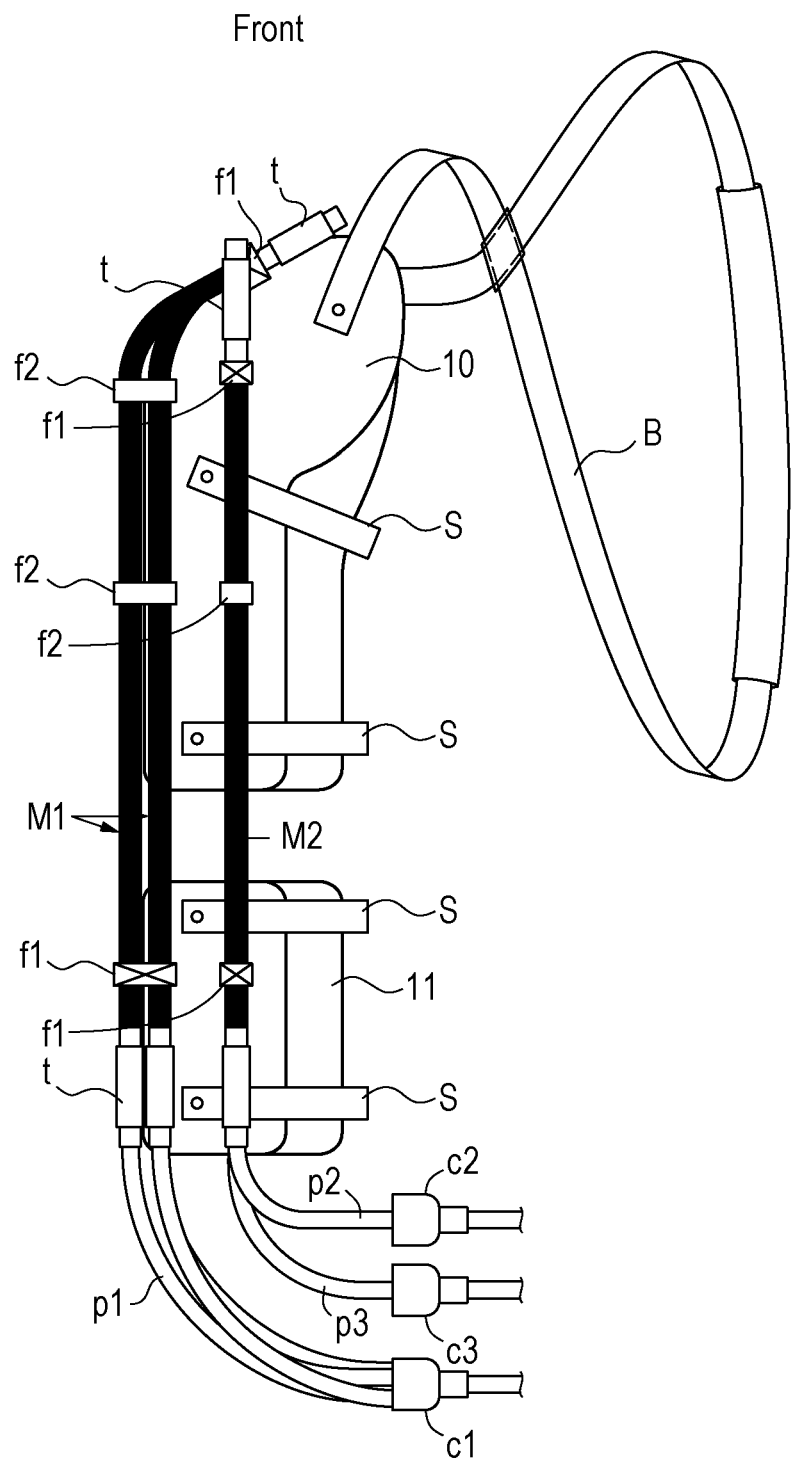
FIG. 6 is a front view of a shoulder brace according to an embodiment.
Figure 7:
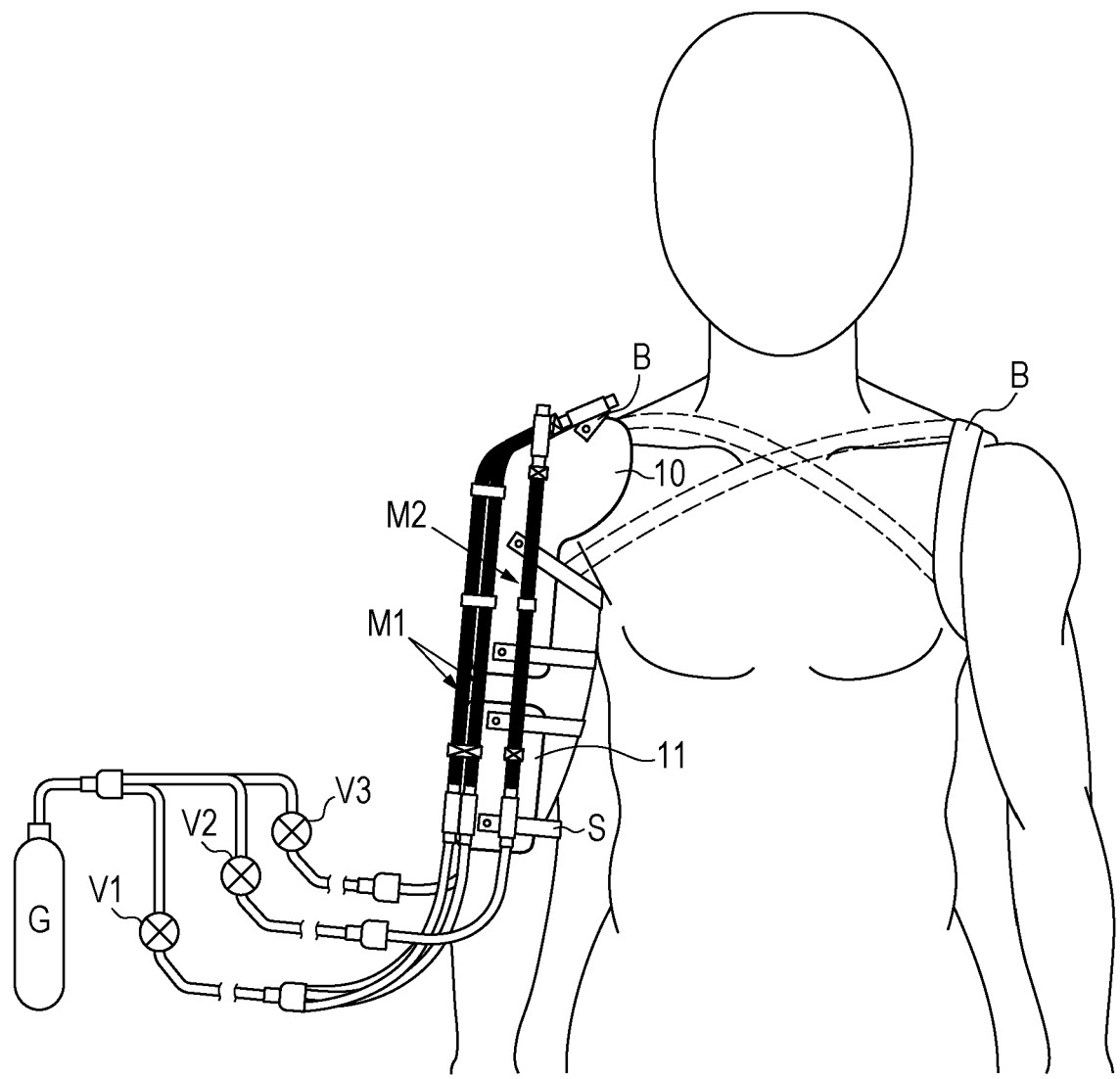
FIG. 7 is a view illustrating a wearing state of a shoulder brace according to an embodiment.

LIST OF REFERENCE NUMERALS 1 shoulder brace
10 shoulder cuff
11 upper arm cuff
M1 main actuator
M2 anterior auxiliary actuator
M3 posterior auxiliary actuator
B belt
S strap
G steel gas cylinder
V1 to V3 pressure adjusting valve
c1 to c3 connector
t terminal
f1 attachment member (fixing)
f2 attachment member (retaining)

What is claimed is:
1. A shoulder brace comprising at least:
a shoulder cuff adapted to cover a shoulder of a user;
an upper arm cuff adapted to cover an elbow joint of the user;
a belt that is adapted to secure the shoulder cuff to the shoulder of the user; and
an actuator made of a Mckibben artificial muscle that can expand and contract in entire length in response to input and output of air pressure applied from an external gas cylinder,
the actuator including
a main actuator adapted to link a side face of the shoulder cuff and a side face of the upper arm cuff across a shoulder joint,
an anterior auxiliary actuator adapted to link a front face of the shoulder cuff and a front face of the upper arm cuff across the shoulder joint, and
a posterior auxiliary actuator adapted to link a back face of the shoulder cuff and a back face of the upper arm cuff across the shoulder joint,
wherein an upper end of the main actuator is fixed at a position on the inner side than the shoulder joint on an upper face of the shoulder cuff.
2. The shoulder brace according to claim 1,
wherein the upper arm cuff comprises a strap and the strap is adapted to immobilize the elbow joint, and
wherein the upper arm cuff has a shape adapted to allow flexion and extension of the elbow joint of the user when worn.

* * * * *